US012768763B2

(12) United States Patent
Wasfy et al.

(10) Patent No.: US 12,768,763 B2
(45) Date of Patent: Oct. 20, 2026

(54) PARTICULATE SENSING SYSTEM AND METHODS FOR DETECTING PARTICULATES IN A FLUID STREAM

(71) Applicant: SPECIALIZED DESANDERS INC., Calgary (CA)

(72) Inventors: Rick Tarik Wasfy, Calgary (CA); Kyle Hierath, Calgary (CA)

(73) Assignee: Specialized Desanders Inc., Calgary (CA)

( * ) Notice: Subject to any disclaimer, the term of this patent is extended or adjusted under 35 U.S.C. 154(b) by 281 days.

(21) Appl. No.: 18/747,724

(22) Filed: Jun. 19, 2024

(65) Prior Publication Data

US 2024/0418621 A1 Dec. 19, 2024

Related U.S. Application Data

(60) Provisional application No. 63/521,827, filed on Jun. 19, 2023.

(51) Int. Cl.
*G01N 15/06* (2024.01)
*G01N 33/28* (2006.01)

(52) U.S. Cl.
CPC ......... *G01N 15/06* (2013.01); *G01N 33/2823* (2013.01); *G01N 33/2835* (2013.01)

(58) Field of Classification Search
CPC ............... G01N 15/06; G01N 33/2823; G01N 33/2835; G01N 2291/02416
See application file for complete search history.

(56) References Cited

U.S. PATENT DOCUMENTS

| | | | |
|---|---|---|---|
| 3,816,773 | A | 6/1974 | Baldwin et al. |
| 3,841,144 | A | 10/1974 | Baldwin |
| 3,844,174 | A | 10/1974 | Chabre et al. |
| 3,906,780 | A | 9/1975 | Baldwin |
| 4,131,815 | A | 12/1978 | Boatright |
| 4,240,287 | A | 12/1980 | Mast et al. |
| 4,296,628 | A | 10/1981 | Mast |
| 4,315,428 | A | 2/1982 | Stuivenwold et al. |

(Continued)

FOREIGN PATENT DOCUMENTS

| | | | |
|---|---|---|---|
| GB | 2619653 | A | 12/2023 |
| WO | 2016/097728 | A1 | 6/2016 |

(Continued)

*Primary Examiner* — Laura Martin Sweeney
*Assistant Examiner* — Anthony W Megna Fuentes
(74) *Attorney, Agent, or Firm* — Gowling WLG (Canada) LLP

(57) ABSTRACT

Provided is a particulate sensing system for detecting particulates in fluid a stream. The system includes a conduit comprising a peripheral wall and defining a fluid passage for conveying a fluid stream therethrough. The system further includes a sensor apparatus comprising a probe body and an acoustic sensor mounted on the probe body. The probe body extends through the peripheral wall. A first end of the probe body is positioned within the fluid passage and a second end of the probe body is external to the conduit. The probe body extends into the fluid passage at a non-perpendicular angle, with a first end face of the probe body tilted toward an upstream direction of the fluid passage. Particulates in the fluid stream impacting the first end face generate an acoustic response in the probe body, which is converted by the acoustic sensor into an electrical output.

20 Claims, 6 Drawing Sheets

(56) References Cited

U.S. PATENT DOCUMENTS

| | | | |
|---|---|---|---|
| 4,674,337 | A | 6/1987 | Jonas |
| 5,257,530 | A | 11/1993 | Beattie et al. |
| 5,419,176 | A | 5/1995 | Walker |
| 5,681,986 | A | 10/1997 | Merk et al. |
| 5,925,972 | A | 7/1999 | Shrader et al. |
| 7,463,158 | B2 | 12/2008 | Hatch et al. |
| 7,578,203 | B2 | 8/2009 | Andersen et al. |
| 7,878,047 | B2 | 2/2011 | Hem blade |
| 8,534,114 | B2 | 9/2013 | Ellson |
| 8,788,222 | B2 | 7/2014 | Friedlander et al. |
| 9,170,240 | B2 | 10/2015 | Lin et al. |
| 10,309,887 | B2 | 6/2019 | Newton et al. |
| 10,698,427 | B2 | 6/2020 | Shah et al. |
| 2007/0047867 | A1 | 3/2007 | Goldner |
| 2011/0301882 | A1 | 12/2011 | Andersen |
| 2018/0120865 | A1 | 5/2018 | Nuryaningsih et al. |
| 2020/0284765 | A1 | 9/2020 | Rustad et al. |
| 2022/0349859 | A1 | 11/2022 | Alberini et al. |

FOREIGN PATENT DOCUMENTS

| | | | |
|---|---|---|---|
| WO | 2018/081687 | A1 | 5/2018 |
| WO | 2024/028735 | A1 | 2/2024 |
| WO | 2024251511 | A1 | 12/2024 |

PARTICULATE SENSING SYSTEM AND METHODS FOR DETECTING PARTICULATES IN A FLUID STREAM

CROSS-REFERENCE TO RELATED APPLICATION

The present application claims a priority benefit to U.S. Provisional Application Ser. No. 63/521,827 filed on Jun. 19, 2023, titled "APPARATUS FOR MEASURING PROPERTIES OF SOLIDS WITHIN A FLUID FLOW", the entire contents of which are incorporated herein by reference in their entirety.

FIELD

Aspects of the present disclosure relate to a system and methods for detecting properties of solids found within a fluid flow stream. More specifically, the disclosure relates to detecting properties of particulates in production fluid during high pressure well operations.

BACKGROUND

Wells are commonly drilled into subterranean formations to extract hydrocarbons. Production fluids from such wells often include particulates such as sand. These particulates can originate from multiple sources including but not limited to: subterranean formations, hydraulic fracturing materials, fluid loss material from drilling mud or fracturing fluids, precipitates and gels formed from chemical stimulation or secondary recovery methods, or a hydrocarbon precipitate due to phase change of produced hydrocarbons caused by changing conditions at the wellbore. As production fluids pass through production equipment, particulates can damage the production equipment by erosive action or plugging the equipment. Erosion of the production equipment can be severe enough to cause catastrophic failure. Thus, frequent cleaning of production equipment is necessitated to reduce events of failure. Particulates may also contaminate surface equipment and production fluids and subsequently inhibit normal operation of oil and gas gathering systems and process facilities. Desanding equipment may, therefore, be used to remove sand or other particulates from fluid (e.g., production fluid) in a well operation.

To optimize the use of desanding equipment to remove sand or other particulates from fluid streams in a well operation, it may be useful to monitor production fluid flow to measure concentration or other properties of particulates in the fluid stream. Some methods of processing output from acoustic sensors to characterize particulates are known, such as those described in U.S. Pat. No. 10,698,427 (Shah, et al.) issued Jun. 30, 2020, or U.S. Patent App. Publication No. US 2018/0120865 (Nuryaningsih, et al.), filed Oct. 31, 2016, the entire contents of which are incorporated herein by reference.

Measurement equipment for detecting properties such as particulate concentration in a fluid stream within a pipe, or any other suitable conduit known in the art, may include a hollow thermocouple probe extending into a fluid stream to measure properties of the fluid stream. Feedthrough equipment may also be used to couple electrical components through a tubular wall. Such conventional probes and feed through equipment may be suitable for low pressure environments but may fail and allow fluid leakage at high pressures. Therefore, there remains a need for measurement apparatuses and systems equipped to detect properties of particulates in a fluid stream during high pressure operations.

SUMMARY

In one aspect, there is provided a particulate sensing system for detecting particulates in a fluid stream, the particulate sensing system comprising: a conduit defining a fluid passage for conveying a fluid stream therethrough and having an upstream fluid inlet end and a downstream fluid outlet end, wherein the conduit comprises a peripheral wall having an inner surface defining the fluid passage and an outer surface; a sensor apparatus comprising a probe body and an acoustic sensor mounted on the probe body, the probe body having a first end and a second end, wherein the probe body extends through the peripheral wall of the conduit such that the first end is positioned within the fluid passage and the second end is external to the conduit; wherein the first end of the probe body defines a first end face, and the probe body extends into the fluid passage at a non-perpendicular angle relative to fluid flow through the conduit, with the first end face of the probe body tilted toward an upstream direction of the fluid passage such that particulates in the fluid stream impacting the first end face generate an acoustic response in the probe body; and wherein the acoustic sensor converts the acoustic response into an electrical output.

In some embodiments, the acoustic sensor is operable to convert vibration responses within the probe body to electrical sensor output.

In some embodiments, the conduit extends in an axial direction, the probe body is a substantially straight rod having a longitudinal axis, and the probe body is positioned with the longitudinal axis of the probe body at a non-perpendicular angle relative to the axial direction of the conduit.

In some embodiments, the second end of the probe body defines a second end face, the first and second end faces are planar, and the first end face is substantially parallel with the second end face; and the acoustic sensor is mounted on the second end face of the probe body.

In some embodiments, the conduit comprises a hole extending through the peripheral wall from the inner surface to the outer surface, and wherein the probe body extends through the hole and is in sealed engagement with the peripheral wall such that the hole is sealed.

In some embodiments, the system further comprises a housing affixed to the outer surface of the conduit and forming a sealed barrier encasing the hole, an entire portion of the probe body exterior to the peripheral wall, and the acoustic sensor.

In some embodiments, the housing comprises a tubular housing section affixed to the peripheral wall of the conduit, and a coupling that attaches to a distal end of the tubular housing section.

In some embodiments, the first end face of the probe body comprises an outer peripheral edge, wherein an upstream side of the peripheral edge of the first end face is adjacent to the inner surface of the peripheral wall.

In some embodiments, the housing comprises electronics configured for receiving the electrical output from the acoustic sensor.

In some embodiments, the probe body comprises a solid bar of material.

In some embodiments, the probe body comprises a split-probe, comprising a first probe body portion affixed to the inner surface of the conduit and a second probe body portion affixed to the outer surface of the conduit, opposite to the first probe body portion, the first portion comprising the first end, and the second portion comprising the second end.

In some embodiments, the non-perpendicular angle of the first end face is less than 90 degrees.

In some embodiments, the non-perpendicular angle of the first end face is between 30 degrees and 60 degrees.

In some embodiments, the non-perpendicular angle of the first end face is 45 degrees.

In another aspect, there is provided a method for detecting particulates in a fluid stream using the particulate sensing system as described herein, the method comprising: passing the fluid stream through the conduit; measuring vibration responses within the probe body by the acoustic sensor, comprising obtaining electrical output from the acoustic sensor, the electrical output being a function of the vibration responses.

In another aspect, there is provided a method for making a particulate sensing system comprising: positioning a probe body of a sensor apparatus such that the probe body extends through a peripheral wall of a conduit, the sensor apparatus comprising the probe body and an acoustic sensor mounted on the probe body, wherein: the conduit comprises a fluid passage for conveying a fluid stream therethrough and having an upstream fluid inlet and a downstream fluid outlet, wherein the conduit comprises a peripheral wall having an inner surface defining a fluid passage for the fluid stream and an outer surface; the conduit comprises a hole extending through the peripheral wall from the inner surface to the outer surface, and positioning the probe body comprises positioning the probe body in a position extending through the hole with a first end of the probe body within the fluid passage and a second end of the probe body external to the peripheral wall; and affixing the probe body to the peripheral wall and sealing the hole with the probe body therein, wherein the first end of the probe body defines a first end face, and the probe body extends into the fluid passage at a non-perpendicular angle relative to fluid flow through the conduit, with the first end face of the probe body tilted toward an upstream direction of the fluid passage.

In some embodiments, the method comprises affixing a housing to the outer surface of the conduit to form a sealed barrier encasing the hole, an entire portion of probe body exterior to the peripheral wall, and the acoustic sensor.

In some embodiments, the method comprises affixing the probe body to the peripheral wall and sealing the hole comprises welding the probe body to the peripheral wall within the hole.

In some embodiments, the first end face of the probe body defines a peripheral edge; and the method further comprises positioning the first end face such that an upstream portion of the peripheral edge in the fluid passage is adjacent to the inner surface of the peripheral wall.

In some embodiments, the probe body comprises a solid body rod, the second end of the probe body comprises a second end face that is parallel to the first end face, and the acoustic sensor is mounted on the second end face.

Other aspects and features of the present disclosure will become apparent, to those ordinarily skilled in the art, upon review of the following description of the specific embodiments of the disclosure.

BRIEF DESCRIPTION OF DRAWINGS

The drawings are primarily for illustrative purposes and are not intended to limit the scope of the inventive subject matter. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 4:
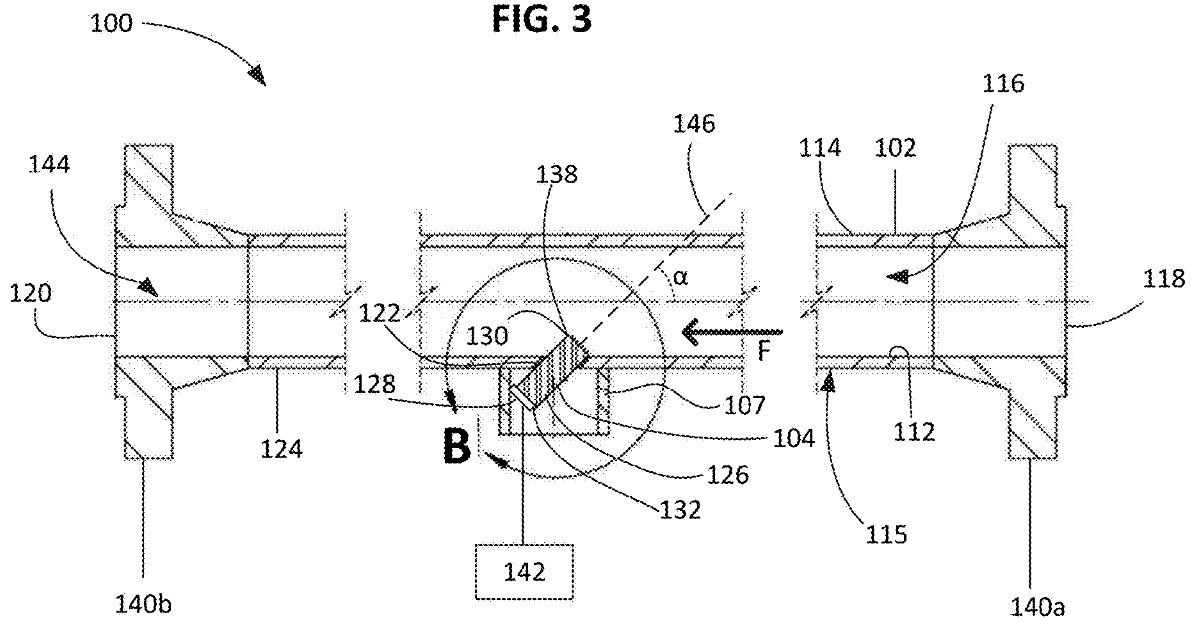
FIG. 4 is a side cross-sectional view of the particulate sensing system taken along the line A-A of FIG. 3.
Figure 5:
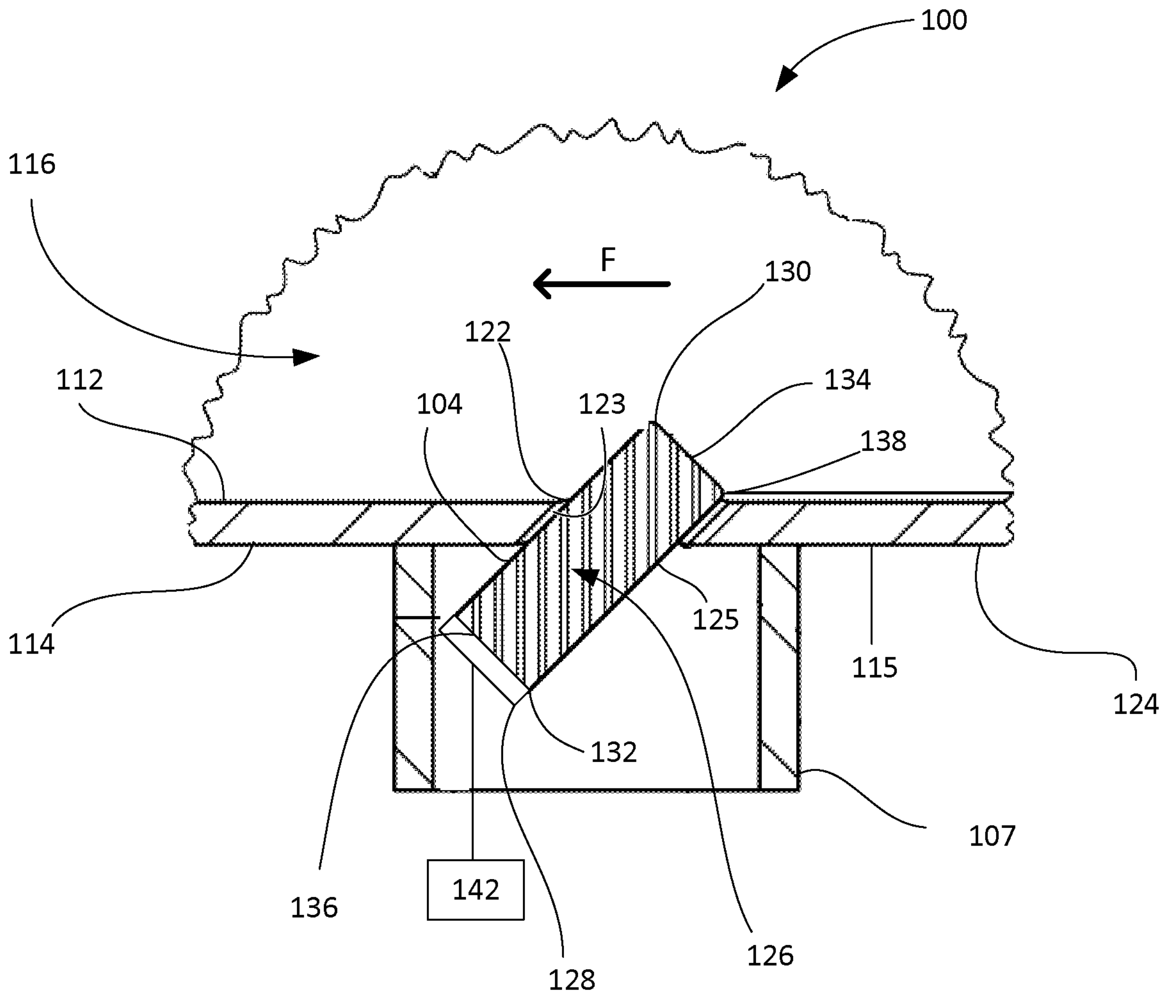
FIG. 5 is an enlarged partial view of the particulate sensing system showing features generally within circle "B" of FIG. 4.

While the embodiments disclosed herein may be modified and/or have alternative forms, specific embodiments thereof have been shown by way of example in the drawings and are herein described in detail. It should be understood, however, that embodiments of the disclosure are not limited to the particular form disclosed, but rather, the disclosure covers all modifications, equivalents, and alternatives of embodiments of the invention as defined by the claims. The angle of a probe body 126 as shown in FIGS. 1, 4 and 5, is not necessarily drawn to scale, and may be positioned at any non-perpendicular angle respective to a longitudinal axis 144 of the conduit 102 as described herein.

According to an aspect of the disclosure, a particulate sensing system is provided for use in measuring one or more properties of solids in a fluid stream. The sensing system comprises a sensor apparatus that is sealingly affixed to a conduit. Properties measurable using the particulate sensing system described herein, may include, but are not limited to, concentration, velocity, or size of particulates such as sand or other solids entrained in the fluid stream. The particulate sensing system may be operable for use for obtaining measurements from a high-pressure fluid stream, such as a high-pressure fluid stream in equipment used for a well operation. Although the example system and methods described herein may be used for measuring properties of fluid streams in high pressure environments, the disclosed principles may be also applied to measuring properties of fluids in low pressure environments. Embodiments are not limited to high pressure applications or to well operations.

The term "particulate sensing" as used herein may refer to detecting one or more properties of particulates in a fluid stream or obtaining sensor signals usable for determining one or more properties of particulates in a fluid stream.

Figure 1:
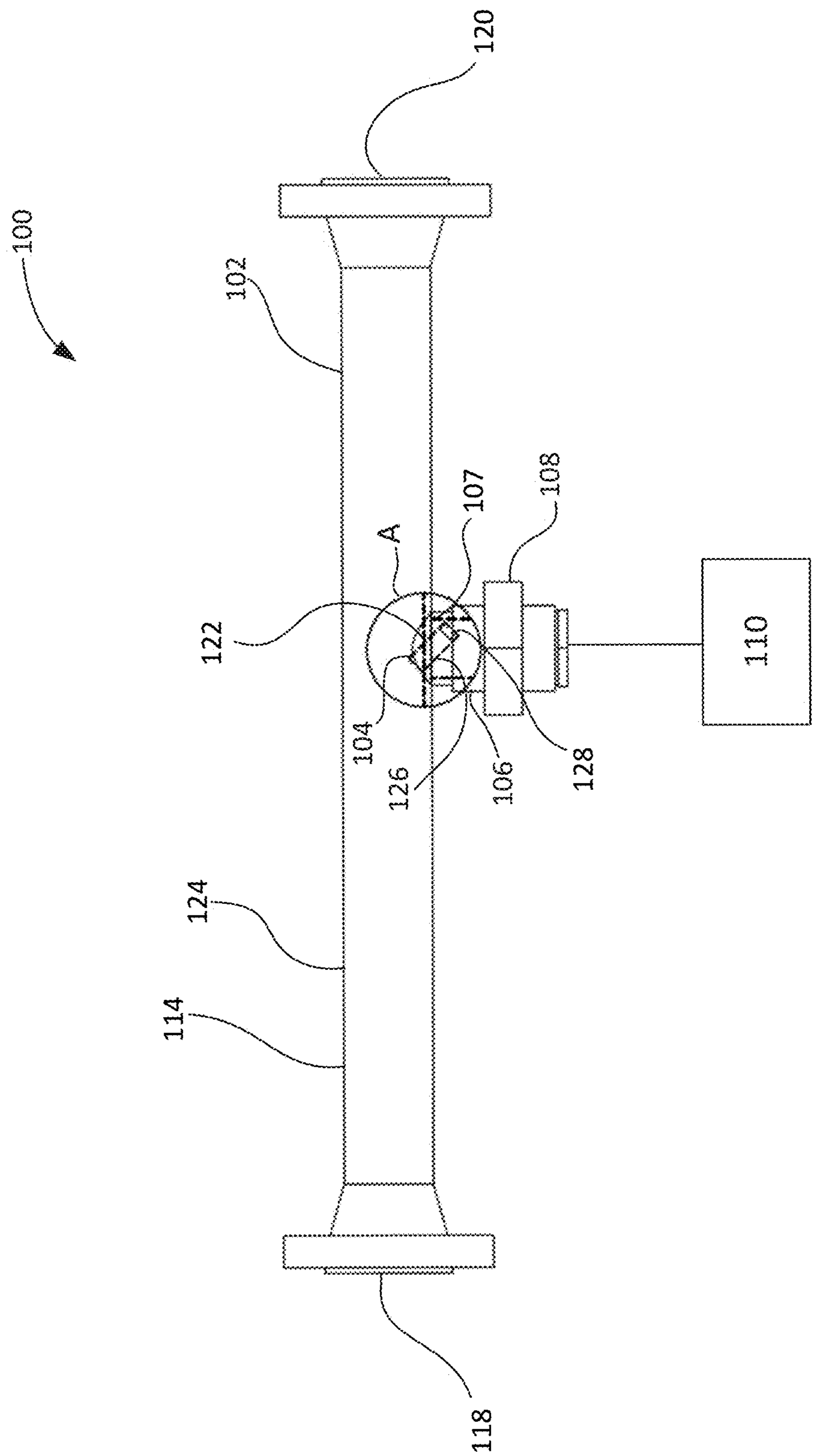
FIG. 1 is a side view of an example particulate sensing system for measuring one or more properties of particulates within a fluid flow according to one or more embodiments disclosed herein.

FIG. 1 illustrates a side view of an embodiment of an example particulate sensing system 100 for detecting and/or measuring one or more properties of particulates in a fluid stream. The fluid stream may be production fluid from a well, or any fluid stream comprising a mixture of gases, liquids, and particulates in any ratio.

The particulate sensing system 100 generally comprises a conduit 102 defining a fluid passage 116 (shown in FIGS. 2 to 5) therethrough for conveying a fluid stream, a sensor apparatus 104, and a housing 106. The conduit 102 comprises a peripheral wall 124 defining the fluid passage 116. The sensor apparatus 104 comprises a probe body 126 and an acoustic sensor 128 mounted on the probe body 126. The probe body 126 extends through the peripheral wall 124 of the conduit 102 such that particulates in a fluid stream passing through the conduit 102 may impact the probe body 126. A first end 130 of the probe body 126 is positioned in the fluid passage 116 and a second end 132 of the probe body 126 is external to the conduit 102. The acoustic sensor 128 mounted to the probe body 126 is also external to the conduit 102. The housing 106 in this embodiment contains the portion of the sensor apparatus 104 that is external to the conduit 102. In other embodiments, the housing 106 may be omitted.

A portion of the conduit 102 and housing 106 within circle "A" is illustrated as transparent (indicated by stippled lines) to show elements within the conduit 102 and housing 106 that would otherwise be hidden from view in FIG. 1.

The particulate sensing system 100 may further include a computing system 110 operatively coupled to the sensor apparatus 104. Alternatively, the computing system 110 may be external to the system or omitted in other embodiments.

Figure 2:
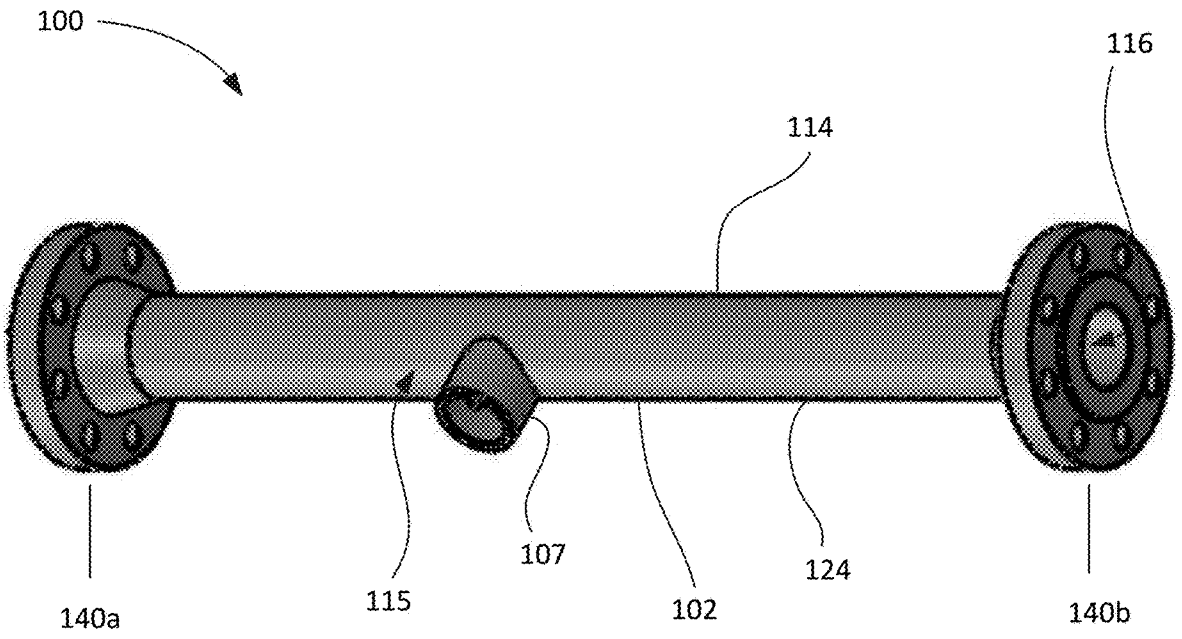
FIG. 2 is a perspective view of a conduit and tubular housing portion of the particulate sensing system of FIG. 1 according to one or more embodiments of the disclosure with a coupling removed.

FIG. 2 is a perspective view of the conduit 102 and a tubular housing section 107 of the housing 106 attached to the conduit 102 according to one or more embodiments.

With reference to FIGS. 1 and 2, the conduit 102 in this embodiment is tubular and comprises a peripheral wall 124 with an inner surface 112 (shown in FIGS. 3 to 5), defining the fluid passage 116 (shown in FIGS. 2 to 5), and an outer surface 114. In this embodiment, the conduit 102 is in the form of a pipe with an inlet end 118 and an outlet end 120 to receive flow of a fluid stream therethrough from the inlet end 118 to the outlet end 120. Fluid flowing through the fluid passage 116 from the inlet end 118 to the outlet end 120 may flow generally in a flow direction that is substantially parallel to a longitudinal axis 144 (shown in FIG. 4) of the conduit 102. In other words, a "downstream direction" may refer to an expected fluid flow direction or path of the fluid passage 116 from the inlet end 118 to the outlet end 120, and an "upstream direction" may refer to a direction along the fluid passage 116 from the outlet end 120 to the inlet end 118 (i.e. a direction heading against or into the flow and opposite to the downstream direction). The term "flow direction" as used herein may refer to the downstream direction of flow generally following a path from the inlet end 118 to the outlet end 120 of the conduit 102. In a pipe, for example, the flow direction may generally flow along a path extending axially through the pipe, while actual fluid flow at a given point in the pipe may vary depending on fluid dynamics and include various flow components and turbulence.

The conduit 102 may be connected, at the inlet end 118 to another conduit or other equipment that delivers the fluid stream to the inlet end 118, and the outlet end 120 may similarly be connected to another conduit or other equipment that receives the fluid stream from the conduit 102. The conduit 102 may be connected inline with a fluid flow system of fluid treatment or well operation equipment, for example. As also shown in FIG. 2, the conduit 102 in this example includes first and second connector flanges (140*a* and 140*b*) at the inlet end 118 and the outlet end 120, respectively, which may be used for connecting the conduit 102 inline with a pipe network or system. However, embodiments of the conduit 102 are not limited to the pipe configuration shown in FIGS. 1 and 2 and may be any other suitable structure with a passage permitting fluid flow therethrough such as a tube, channel, groove, or duct. Embodiments are also not limited to flange connectors or any other particular structure or method for connecting the conduit 102 to other equipment.

Figure 3:
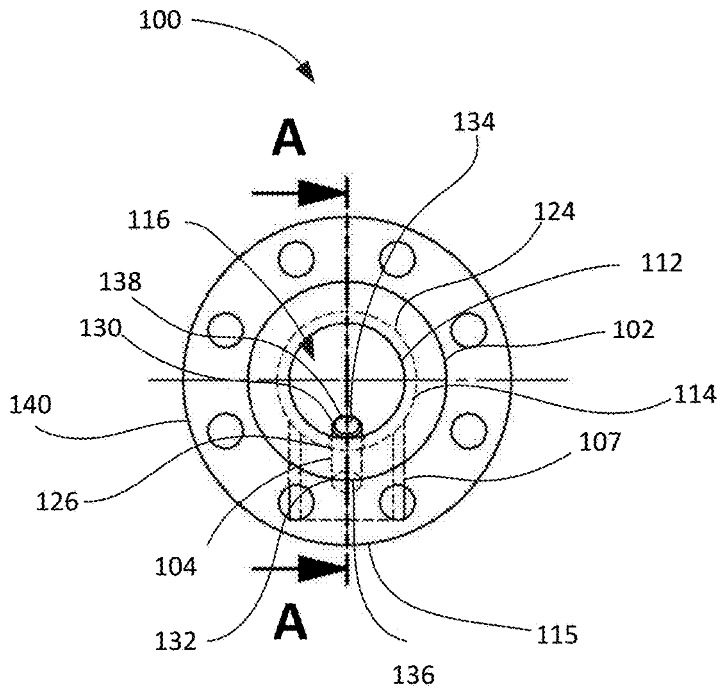
FIG. 3 is an end view of the particulate sensing system of FIGS. 1 and 2 according to one or more embodiments of the disclosure.

FIG. 3 is an end view of the particulate sensing system 100 of FIGS. 1 and 2 according to one or more embodiments of the disclosure. FIG. 4 is a side cross-sectional view of the particulate sensing system 100 taken along the line A-A of FIG. 3. FIG. 5 is an enlarged partial view of the particulate sensing system 100 showing features generally within circle "B" of FIG. 4.

With reference to FIGS. 3 to 5, the sensor apparatus 104 includes the probe body 126 and the acoustic sensor 128 coupled to the probe body 126. The term "probe body" as used herein may refer to any body structure suitable for carrying out the principles as described herein, and may include a receptor, a rod, a bar, or a shaft, among other suitable embodiments. The probe body 126 shown in FIGS. 3 to 5 has a generally cylindrical rod shape, but embodiments are not limited to this configuration. The size, diameter, and/or length of the probe body 126 may also vary.

Fluid may flow generally along from the inlet end 118 to the outlet end 120 in the downstream direction indicated by the arrow labeled "F" shown in FIG. 4. As the fluid stream travels through the fluid passage 116, sand or other particulates within the fluid are incident on a first end face 134 of the probe body 126 and may cause vibrations or another measurable response in the probe body 126. The vibrations may travel through the probe body 126 to the acoustic sensor 128.

The probe body 126 in this example embodiment comprises a first end 130 having the first end face 134 and a second end 132 having a second end face 136 (shown in FIG. 3). The probe body 126 is straight, such that the first end 130 is opposite the second end 132. In this embodiment, the first end face 134 and the second end face 136 are substantially planar. The first end face 134 and the second end face 136 are parallel to and opposite one another. The first end 130 comprises a peripheral edge 138 extending about the circumference of the first end face 134.

The acoustic sensor 128 is affixed to the second end face 136, although the placement of the acoustic sensor 128 may vary in other embodiments. The acoustic sensor 128 generates electrical signal outputs as a function of acoustic responses (e.g. vibrations) in the probe body 126. The acoustic sensor 128 may be a piezoelectric sensor or any other sensor suitable for generating electrical output as a function of acoustic responses.

The conduit 102 further defines a hole 122 through the peripheral wall 124 configured to receive the sensor apparatus 104 therethrough. The probe body 126 extends through the hole 122 and partially extends into the fluid passage 116 of the conduit 102. The first end 130 of the probe body 126 is positioned in the fluid passage 116, and the second end 132 of the probe body 126 remains external to the conduit 102. Impacts of particulates within the fluid passage 116 on the first end face 134 of the probe body 126 may generate acoustic responses in the probe body 126.

The first end face 134 of the probe body 126 is angled to partially face into the upstream direction (i.e. partially facing into the fluid flow). With the cylindrical probe body 126 in this example embodiment, this angled orientation of the first end face 134 is provided by positioning the probe body 126 at a non-perpendicular angle respective to the longitudinal axis 144 of the conduit 102. The cylindrical probe body 126 has a longitudinal axis 146 (shown in FIG. 4), with the first and second end faces (134 and 136) being approximately perpendicular to the longitudinal axis 146 of the probe body 126. The longitudinal axis 146 of the probe body 126 is at a non-perpendicular angle to the longitudinal axis 144 of the conduit 102. FIG. 4 illustrates angle "a" between these two longitudinal axes (144 and 146). The non-perpendicular angle between the longitudinal axis 144 of the conduit 102 and the longitudinal axis 146 of the probe body 126 may be less than 90 degrees. In some embodiments, the angle is between 1 degree and 89 degrees. In some embodiments, the angle is between 15 and 75 degrees. In some embodiments, the angle is between 30 degrees and 60 degrees. In the embodiment shown in FIGS. 1 to 5, the probe body 126 is set at an angle of approximately 45 degrees relative to the longitudinal axis 144 of the conduit 102. In other words, the first end face 134 of the probe body 126 is approximately at a 45 degree angle relative to the axial direction of the inner surface 112 of the peripheral wall 124, although this angle may vary in other embodiments. The specific angle may be selected based on factors such as fluid stream properties, expected particulate characteristics, properties of the conduit 102, and/or other factors, and embodiments are not limited to a particular angle.

The vibrations generated by the particulates impacting the first end face 134 travel through the probe body 126 from the first end 130 to the second end 132. Beneficially, the shape of the probe body 126, being straight with parallel first and second end faces (134 and 136), may facilitate vibrational responses travelling from the first end face 134 to the second end face 136. Thus, impacts on the first end face 134 may generate a stronger direct acoustic response at the second end face 136. The acoustic sensor 128 is configured to detect these vibrations and generate the corresponding electrical output.

The acoustic sensor 128 may detect vibrations in the sonic or ultrasonic frequency range, for example. Particulates in the fluid stream may also cause other measurable responses in the probe body 126, and embodiments are not limited to the acoustic sensor 128 detecting vibrations, or vibrations in a particular frequency range.

Non-cylindrical rod shapes (e.g. rectangular prism) may similarly be positioned relative to the conduit 102 to provide a face in the fluid passage 116 angled to face at least partially upstream. In other embodiments, the probe body 126 may have another non-cylindrical and/or non-rod shape and may still provide a face that is angled into the flow within the fluid passage 116.

The sensor apparatus 104 may be positioned such that the first end 130 of the probe body 126 intrudes as minimally as possible into the fluid passage 116. For example, in the embodiment shown in FIGS. 3 to 5, a point along the peripheral edge 138 of the first end face 134 is adjacent or nearly adjacent to the inner surface 112, such that the point is tilted towards an upstream direction of the fluid passage 116. This may, for example, optimize fluid flow through the fluid passage 116 or permit a constant flow rate throughout the fluid passage 116. Nevertheless, a person skilled in the art may combine varying non-perpendicular angles and degrees of intrusion into the fluid passage 116 to accommodate different fluid viscosity, pressure, concentration, other properties of the fluid stream, or other application considerations.

The first end face 134, being angled towards an upstream direction of the fluid passage 116 with a point of the peripheral edge 138 adjacent or abutting the inner surface 112 of the conduit 102, may essentially form a ramp or ramp-like configuration within the fluid passage 116. This configuration may prevent particulates from becoming lodged between the first end 130 and the inner surface 112 of the conduit 102 and may facilitate consistent fluid flow over the first end face 134 while still exposing the first end face 134 to impacts from particulates in the fluid stream.

Referring to FIGS. 1 through 5, the probe body 126 is positioned at or near a bottom 115 of the conduit 102 (i.e. the probe body 126 extends through a bottom portion of the peripheral wall 124). Due to gravitational forces, increased particulates may be found at the bottom 115 of the conduit 102 in a fluid stream. Thus, positioning the sensor apparatus 104 at the bottom 115 of the conduit 102 may beneficially place the probe body 126 in an area of the fluid stream with a higher concentration of particulates. However, the probe body 126 may be at other positions about the circumference of the conduit 102 in other embodiments.

As best shown in FIG. 5, the hole 122 in this example embodiment extends through the peripheral wall 124 at the same angle as the probe body 126. That is, a side wall 123 of the hole 122 matches the angle of the side peripheral surface 125 of the probe body 126. The hole 122 may be sized to form a friction fit with the probe body 126, or the hole 122 may be slightly larger than the probe body 126.

The probe body 126 may be welded to the conduit 102 (within the hole 122) such that the hole 122 is sealed to prevent fluid flow therethrough and withstand pressure in the conduit 102. This may prevent damage of electronics 142 (shown in FIGS. 4 and 5 and discussed below) in the housing 106, as well as increase safety. Welding may provide a seal with sufficient structural integrity to withstand high pressure fluid flow within the conduit 102. This may maintain steady fluid pressure within the conduit 102 and prevent damage of electronics 142 in the housing 106 by preventing fluid flow from the fluid passage 116 from passing through the hole 122. The probe body 126 may comprise the same material as the peripheral wall 124 of the conduit 102. The welded seal around the probe body 126 may reduce vibrational noise in the probe body 126 originating from particulates striking the conduit 102, in comparison to an embodiment where the probe and conduit are formed from a single contiguous piece of material. The welded seal may function as a boundary around the probe body 126 that may diminish such noise to a degree. Embodiments are not limited to welding and other methods of securing the probe body 126 in the hole 122 may be used. For instance, for use in low pressure environments, the hole 122 may be sealed with an o-ring or by other conventional methods known in the art.

The housing 106 in this embodiment is affixed to the outer surface 114 of the conduit 102 and encloses the second end 132 of the probe body 126 and the acoustic sensor 128. The housing 106 may be configured to provide a sealed barrier or an outer boundary to protect the probe body 126 and the acoustic sensor 128. The housing 106 may also be configured to withstand fluid pressure within the conduit 102 in the event that pressurized fluid from the conduit 102 breaches the hole 122 or otherwise enters the housing 106.

As illustrated in FIG. 1, the housing 106 in this embodiment comprises a tubular housing section 107 and a coupling 108 that may be removably attached to a distal end of the tubular housing section 107. The coupling 108 may be threaded onto the tubular housing section 107, or alternative conventional methods known in the art to securely attach two members may be used. The tubular housing section 107 and the coupling 108 create an outer boundary and may provide an intrinsic safe sealed barrier surrounding the second end 132 of the probe body 126 and the acoustic sensor 128. The housing 106 may provide, for example, an explosion proof environment suitable for operations at high pressure applications.

The system 100 may optionally further comprise electronics 142 (shown in FIGS. 4 and 5) coupled to the sensor apparatus 104. More particularly, the electronics 142 may be coupled to the acoustic sensor 128. The electronics 142 may comprise circuitry configured to receive output (e.g. electrical signals) from the acoustic sensor 128 and to transmit electrical output to the computing system 110. For example, the electronics 142 may be connected to the computing system 110 by a wired or wireless communication. In some embodiments, the electronics 142 may include hardware and/or software for performing processing on the output from the acoustic sensor 128. The electronics 142 may be contained within the housing 106, within one or both of the tubular housing section 107 and the coupling 108. The acoustic sensor 128 may be situated within the tubular housing section 107 and/or the coupling 108, depending on the length of the probe body 126 and the non-perpendicular angle of the probe body 126. The electronics 142 may comprise, for example, one or more transmitters, a processor, memory having computer-executable instructions stored thereon for performing any of the potential functions of the electronics 142 discussed above; or any other combination of hardware and/or software.

Electronics 142 for receiving electrical output from the acoustic sensor 128 may be coupled to the computing system 110 for processing the electrical output. Alternatively, output from the acoustic sensor 128 or from the electronics 142 may be communicated to a remote computing device via wired or wireless communications. In another embodiment, there may be no need for a tubular housing section 107 or coupling 108, and a wire may extend from the acoustic sensor 128 to communicate the electrical signal to a computing system 110. Electrical output from the acoustic sensor 128 may be processed to determine concentration or other properties of particulates within the fluid flow. Other properties may, for example, include particulate size or particulate velocity within the fluid flow.

While the embodiment shown in FIGS. 1 to 5 illustrates the one sensor apparatus 104 affixed to the conduit 102, a plurality of sensor apparatuses 104 may be affixed to the conduit 102 at different respective positions. For example, a plurality of apparatuses may be spaced along the length and/or circumference of the conduit 102. For example, if the conduit 102 is oriented in a horizontal direction, the sensor apparatus 104 may be situated at the bottom 115 of the conduit 102, or at the 3 o'clock or 9 o'clock positions. Other sensor apparatus 104 positions may also be used.

As shown in FIGS. 2 to 5, the shape of the tubular housing section 107 is cylindrical, although embodiments are not limited to this configuration. The housing 106 may have other shapes and configurations.

The probe body 126 comprises a solid body. The term "solid body" is generally used herein to encompass any body with an absence of hollow spaces therein. The probe body 126 may comprise the same material as the conduit 102. The material may be a metal such as solid steel. Any suitable material such as solid bar stock may be used. The solid nature of the probe body 126 may increase integrity of the system 100 in high pressure environments. Pressure within the conduit 102 may, for example, be 10,000 PSI or more. For instance, if the first end 130 of the probe body 126 was severed along the inner surface 112, the fluid passage 116 would remain sealed and prevent leakage, while holding the full pressure of the conduit 102. A hollow probe body, by contrast, which becomes severed or otherwise damaged at high pressures may allow fluid to enter the electronics 142 directly and leak into the environment. By welding the solid probe body 126 to the conduit 102, the risk of unwanted release may be reduced or eliminated. There may also be a benefit of noise reduction and minimized signal reflection inside the solid probe body 126, thus increasing the sensitivity and accuracy of the acoustic sensor 128.

In still some other embodiments, the probe body 126 may comprise a split probe body having a first probe portion welded to the inner surface 112 of the conduit 102 and a second probe portion welded to the outer surface 114 of the conduit 102, opposite to the first portion. Together, the first and second probe body portions may be aligned to approximate or simulate a single continuous probe body. However, the solid probe body 126 of FIGS. 1 to 5 may, however, have reduced noise compared to a split probe body. For example, a split probe body may generate increased signal reflections caused by material interfaces where the peripheral wall 124 splits the probe body 126.

Embodiments are not limited to the sensor apparatus 104 positioning or configuration shown in the drawings and specifically described herein. Other configurations, positioning, and/or orientation may be used while still allowing detection of a measurable response, such as vibrations from particulates striking the first end face 134 of the probe body 126.

Dimensions of components of the particulate sensing system 100, including the conduit 102 and the acoustic sensor 128, may vary and embodiments are not limited to any particular dimension. By way of example, the conduit 102 may comprise a pipe having an outer diameter of approximately 2 to 24 inches and an overall length of approximately 1 to 6 feet. In some embodiments, the outer diameter of the conduit 102 may be between 2 to 4 inches. The conduit 102 may be configured to withstand high pressures, such as 10,000 PSI, and high fluid flows in well operations. The probe body 126 may be a cylindrical member that is approximately 2 inches long with an outer diameter of approximately ¾ inches. The housing 106 may, for example, have an outer diameter of approximately 3 inches and a height of approximately 2 inches. However, these are only examples and do not limit the dimensions of these components, which may vary.

Figure 6:
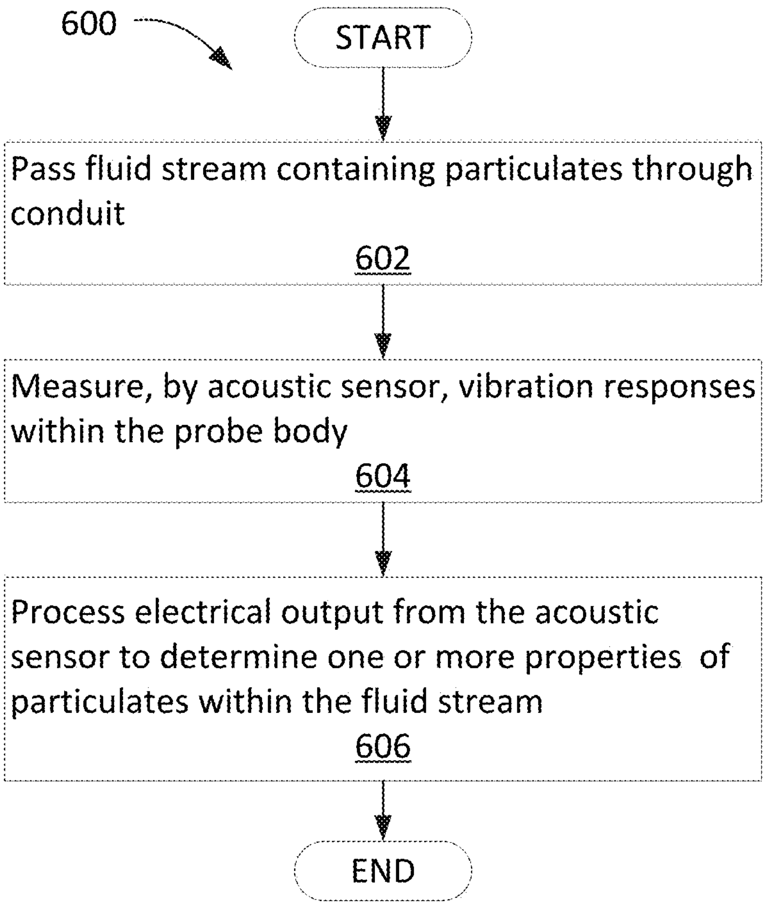
FIG. 6 is a flowchart of a method for detecting particulates in a fluid stream using the particulate sensing system described herein according to some embodiments.

FIG. 6 is a flowchart of a method 600 for detecting particulates in a fluid stream using the particulate sensing system 100 described herein according to some embodiments. For illustrative purposes, the method 600 is described with reference to the example system 100 shown in FIGS. 1 to 5, but methods are not limited to that particular system 100.

At step 602, a fluid stream containing particulates is passed through the conduit 102. For example, the conduit may be connected inline with a pipe system, and the fluid stream may be within that pipe system and pass through the conduit 102.

At step 604, vibration responses within the probe body 126 are measured by the acoustic sensor 128 mounted on the probe body 126. Measuring the vibration responses may comprise obtaining electrical output from the acoustic sensor 128. The electrical output may be a function of the vibration responses.

Optionally, at step 606, the electrical output from the acoustic sensor 128 is processed to determine one or more properties of the particulates within the fluid stream. The processing may, for example, be performed by the computing system 110 using methods of processing data known in the art. The electronics 142 shown in FIGS. 4 and 5 may perform a part or all of processing. The processing may also, for example, be performed by a combination of the electronics 142 and the computing system 110.

The method 600 of FIG. 6 may also include additional steps or features described above or below herein.

Figure 7:
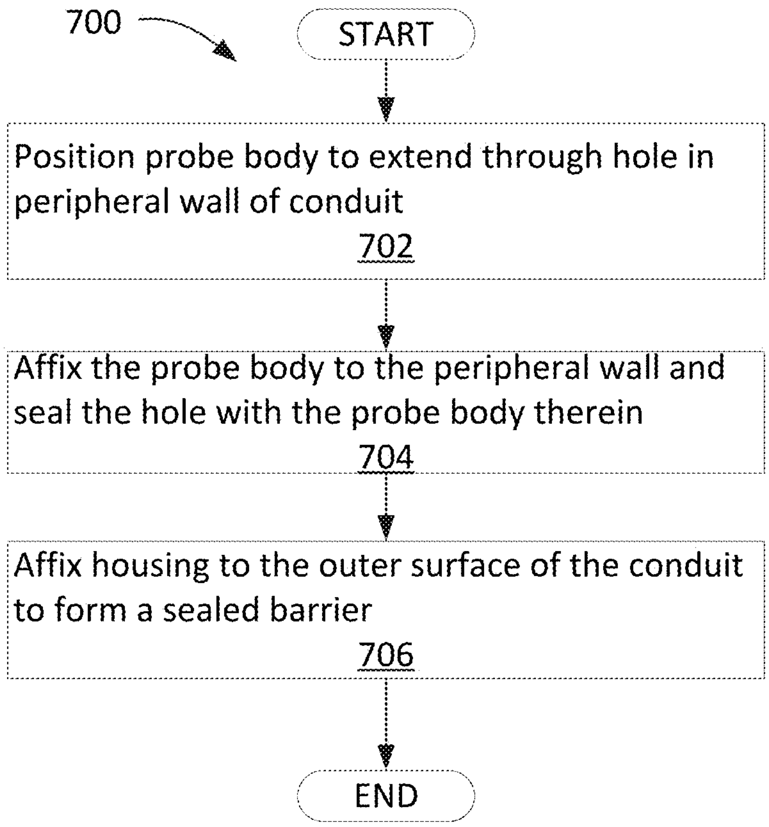
FIG. 7 is a flowchart of a method for making a particulate sensing system described herein according to some embodiments.

FIG. 7 is a flowchart of a method 700 for making a particulate sensing system 100 described herein according to some embodiments. For illustrative purposes, the following description of the method 700 makes reference to components of the example system 100 shown in FIGS. 1 to 5, but methods are not limited to that particular system 100.

Optionally, at step 702, a conduit and a sensor apparatus comprising a probe body 126 and an acoustic sensor 128 as described herein is provided. The conduit may be in the form of the example conduit 102 of the system 100 of FIGS. 1 to 5. The sensor apparatus may be in the form of the example sensor apparatus 104 of the system 100 of FIGS. 1 to 5. Providing the conduit 102 and the sensor apparatus 104 may comprise purchasing, making, and/or otherwise obtaining the conduit 102 and the sensor apparatus 104.

At step 702, the probe body 126 is positioned so that the probe body 126 extends through the peripheral wall 124 of the conduit 102. Positioning the probe body 126 may comprise positioning the probe body 126 such that it extends through a hole 122 in the peripheral wall 124 with a first end 130 of the probe body 126 within the fluid passage 116 and a second end 132 of the probe body 126 external to the peripheral wall 124.

The probe body 126 may be positioned such that a first end face 134 of the probe body 126 is oriented at an angle to face partially upstream within the fluid passage 116.

At step 704, the probe body 126 is affixed to the peripheral wall 124 and the hole 122 is sealed with the probe body 126 therein.

Affixing the probe body 126 to the peripheral wall 124 and sealing the hole 122 may comprise welding the probe body 126 to a side wall 123 of the hole 122.

Optionally, at step 706, a housing (such as the housing 106 of the system 100 in FIGS. 1 to 5) is affixed to the outer surface 114 of the conduit 102 to form a sealed barrier encasing the hole 122, the second end 132 of the probe body 126 external to the peripheral wall 124, and the acoustic sensor 128.

The method 700 of FIG. 7 may also include additional steps or features described above or below herein.

Figure 8:
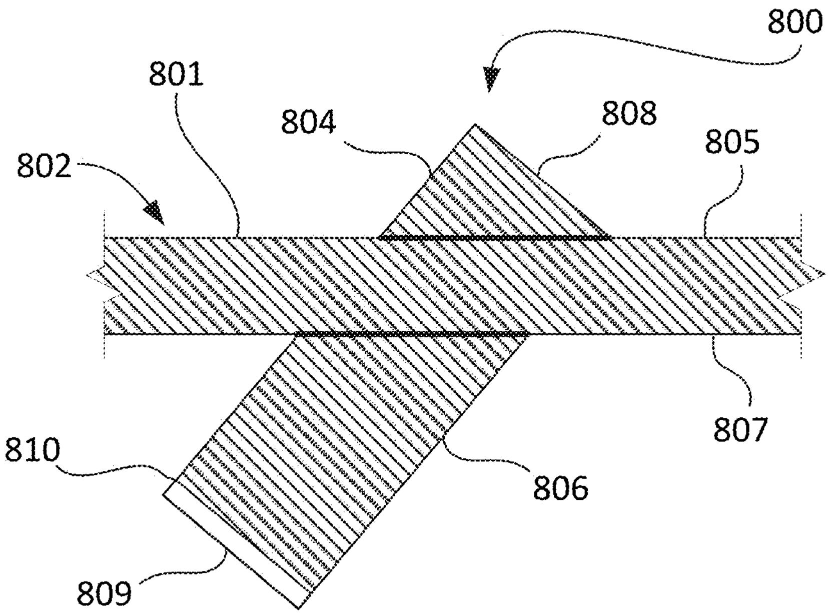
FIG. 8 is a partial cross-sectional side view of a split probe body mounted to a peripheral wall of a conduit.

FIG. 8 is a partial cross-sectional side view of a split-probe 800 mounted to a peripheral wall 801 of a conduit 802 according to some embodiments. The split-probe 800 comprises a first probe body portion 804 affixed to the inner surface 805 of the conduit 802 and a second probe body portion 806 affixed to the outer surface 807 of the conduit 802, opposite to the first probe body portion 804. The first and second body portions 804 and 806 may be welded to the peripheral wall 801, for example. The first and second body portions 804 and 806 are aligned as a split-rod shape that is at a non-perpendicular angle to the flow or conduit 802, with the first end face 808 of the first probe body portion 804 angled into the flow, similar to the embodiment of FIGS. 1 to 5. However, the peripheral wall 801 splits the probe 800 in this embodiment. Acoustic sensor 809 of the probe 800 (external to the conduit 802) is also shown in FIG. 8 attached to second end face 810 of the second probe body portion 806 (opposite to the first end face 808). In some embodiments, the probe body and peripheral wall may formed as a unitary body.

It is understood that a combination of more than one of the embodiments described above may be implemented. Embodiments are not limited to any particular one or more of the approaches, methods or apparatuses disclosed herein. One skilled in the art will appreciate that variations and alterations of the embodiments described herein may be made in various implementations without departing from the scope of the claims.

What is claimed is:

1. A particulate sensing system for detecting particulates in a fluid stream, the particulate monitoring system comprising:

a conduit defining a fluid passage for conveying a fluid stream therethrough and having an upstream fluid inlet end and a downstream fluid outlet end, wherein the conduit comprises a peripheral wall having an inner surface defining the fluid passage and an outer surface;

a sensor apparatus comprising a probe body and an acoustic sensor mounted on the probe body, the probe body having a first end and a second end, wherein the probe body extends through the peripheral wall of the conduit such that the first end is positioned within the fluid passage and the second end is external to the conduit;

wherein the first end of the probe body defines a first end face, and the probe body extends into the fluid passage at a non-perpendicular angle relative to fluid flow through the conduit, with the first end face of the probe body tilted toward an upstream direction of the fluid passage such that particulates in the fluid stream impacting the first end face generate an acoustic response in the probe body; and wherein the acoustic sensor converts the acoustic response into an electrical output.

2. The system of claim 1, wherein the acoustic sensor is operable to convert vibration responses within the probe body to the electrical output.

3. The system of claim 1, wherein the conduit extends in an axial direction, the probe body is a substantially straight rod having a longitudinal axis, and the probe body is positioned with the longitudinal axis of the probe body at the non-perpendicular angle relative to the axial direction of the conduit.

4. The system of claim 1, wherein:

the second end of the probe body defines a second end face, the first and second end faces are planar, and the first end face is substantially parallel with the second end face; and the acoustic sensor is mounted on the second end face of the probe body.

5. The system of claim 1, wherein the conduit comprises a hole extending through the peripheral wall from the inner surface to the outer surface, and wherein the probe body extends through the hole and is in sealed engagement with the peripheral wall such that the hole is sealed.

6. The system of claim 5, further comprising a housing affixed to the outer surface of the conduit and forming a sealed barrier encasing the hole, an entire portion of the probe body exterior to the peripheral wall, and the acoustic sensor.

7. The system of claim 6, wherein the housing comprises a tubular housing section affixed to the peripheral wall of the conduit, and a coupling that attaches to a distal end of the tubular housing section.

8. The system of claim 6, wherein the housing comprises electronics configured for receiving the electrical output from the acoustic sensor.

9. The system of claim 1, wherein the first end face of the probe body comprises an outer peripheral edge, wherein an upstream side of the peripheral edge of the first end face abuts the inner surface of the peripheral wall.

10. The system of claim 1, wherein the probe body comprises a solid bar of material.

11. The system of claim 1, wherein the probe body comprises a split-probe, comprising a first probe body portion affixed to the inner surface of the conduit and a second probe body portion affixed to the outer surface of the conduit, opposite to the first probe body portion, the first portion comprising the first end, and the second portion comprising the second end.

12. The system of claim 1, wherein the non-perpendicular angle of the first end face is less than 90 degrees.

13. The system of claim 1, wherein the non-perpendicular angle of the first end face is between 30 degrees and 60 degrees.

14. The system of claim 1, wherein the non-perpendicular angle of the first end face is 45 degrees.

15. A method for detecting particulates in a fluid stream using the system of claim 1, the method comprising:

passing the fluid stream through the conduit;

measuring vibration responses within the probe body by the acoustic sensor, comprising obtaining electrical output from the acoustic sensor, the electrical output being a function of the vibration responses.

16. A method for making a particulate sensing system comprising:

positioning a probe body of a sensor apparatus such that the probe body extends through a peripheral wall of a conduit, the sensor apparatus comprising the probe body and an acoustic sensor mounted on the probe body, wherein:

the conduit comprises a fluid passage for conveying a fluid stream therethrough and having an upstream fluid inlet and a downstream fluid outlet, wherein the conduit comprises a peripheral wall having an inner surface defining a fluid passage for the fluid stream and an outer surface;

the conduit comprises a hole extending through the peripheral wall from the inner surface to the outer surface, and positioning the probe body comprises positioning the probe body in a position extending through the hole with a first end of the probe body within the fluid passage and a second end of the probe body external to the peripheral wall; and affixing the probe body to the peripheral wall and sealing the hole with the probe body therein, wherein the first end of the probe body defines a first end face, and the probe body extends into the fluid passage at a non-perpendicular angle relative to fluid flow through the conduit, with the first end face of the probe body tilted toward an upstream direction of the fluid passage.

17. The method of claim 16, further comprising affixing a housing to the outer surface of the conduit to form a sealed barrier encasing the hole, an entire portion of probe body exterior to the peripheral wall, and the acoustic sensor.

18. The method of claim 16, wherein affixing the probe body to the peripheral wall and sealing the hole comprises welding the probe body to the peripheral wall within the hole.

19. The method of claim 16, wherein the first end face of the probe body defines a peripheral edge; and the method further comprises positioning the first end face such that an upstream portion of the peripheral edge in the fluid passage is adjacent to the inner surface of the peripheral wall.

20. The method of claim 16, wherein probe body comprises a solid body rod, the second end of the probe body comprises a second end face that is parallel to the first end face, and the acoustic sensor is mounted on the second end face.

* * * * *